(12) United States Patent
O'Brien et al.

(10) Patent No.: US 11,918,263 B2
(45) Date of Patent: Mar. 5, 2024

(54) MIXED MATERIALS BONE SCREW

(71) Applicants: Stephen James O'Brien, New York, NY (US); Thomas Zink, San Antonio, TX (US)

(72) Inventors: Stephen James O'Brien, New York, NY (US); Thomas Zink, San Antonio, TX (US)

( * ) Notice: Subject to any disclaimer, the term of this patent is extended or adjusted under 35 U.S.C. 154(b) by 124 days.

(21) Appl. No.: 16/952,146

(22) Filed: Nov. 19, 2020

(65) Prior Publication Data
US 2021/0145495 A1 May 20, 2021

Related U.S. Application Data

(60) Provisional application No. 62/937,317, filed on Nov. 19, 2019.

(51) Int. Cl.
| | |
|---|---|
| *A61B 17/86* | (2006.01) |
| *A61B 17/80* | (2006.01) |
| *A61B 17/88* | (2006.01) |
| *A61L 31/02* | (2006.01) |

(52) U.S. Cl.
CPC ........ *A61B 17/864* (2013.01); *A61B 17/8057* (2013.01); *A61B 17/863* (2013.01); *A61B 17/8635* (2013.01); *A61B 17/8811* (2013.01); *A61L 31/022* (2013.01)

(58) Field of Classification Search
CPC ............................. A61B 17/864; A61B 17/866
See application file for complete search history.

(56) References Cited

U.S. PATENT DOCUMENTS

| | | | | |
|---|---|---|---|---|
| 2009/0157123 | A1* | 6/2009 | Appenzeller | A61B 17/68 606/301 |
| 2020/0367951 | A1* | 11/2020 | Rocci | A61B 17/8057 |

* cited by examiner

*Primary Examiner* — Olivia C Chang
(74) *Attorney, Agent, or Firm* — Brennan, Manna & Diamond, LLC

(57) ABSTRACT

The present invention relates to a mixed material bone screw. The bone screw comprises a distal end made of a biocompatible material and a proximal end made from a stronger material to resist stripping of the bone screw during its insertion or removal from a bone. In another embodiment, the mixed material bone screw is cannulated, wherein the bone screw has a bore forming a central channel connected to a plurality of sideward channels for delivering bone cement or other substances into the bone surrounding the bone screw.

8 Claims, 2 Drawing Sheets

MIXED MATERIALS BONE SCREW

CROSS-REFERENCE TO RELATED APPLICATION

The present application claims priority to, and the benefit of, U.S. Provisional Application No. 62/937,317, which was filed on Nov. 19, 2019 and is incorporated herein by reference in its entirety.

FIELD OF THE INVENTION

The present invention relates generally to a surgical bone screw comprised of a plurality of materials. More specifically, the bone screw comprises a distal end made from a first biocompatible material, and a proximal end made from a second material that is relatively stronger/stiffer than the biocompatible material. Accordingly, the present specification makes specific reference to the presently described invention. However, it is to be appreciated that certain aspects of the present invention are also equally amenable to other like applications, devices and methods of manufacture.

BACKGROUND

By way of background, bone screws generally comprise an implantable screw capable of internal fixation or anchoring, and can be used to surgically correct many types of injuries or deformities including, without limitation, scoliosis, kyphosis and the like. Bone screws can also be used to repair a fracture, or to secure rods, plates or nails, and can be permanent, semi-permanent or bio-degradable. For example, a bone screw may be left in place after a patient heals, or the bone screw may be surgically removed.

Different types of implants (e.g., screws, pins, rods) are sometimes used in spinal surgery to help fix the spine into a more normal position, and to stabilize a specific area of the spinal column. For example, a cortical screw is a type of bone screw designed to screw into bony prominences of the posterior vertebra or other bone where dense cortical bone is predominantly present. By comparison, a cancellous bone screw, which has a different thread pattern, is sometimes used during surgery to secure the anterior vertebra or other bone where porous cancellous bone is present in greater quantity. Functioning as firm anchor points, two or more bone screws can be interconnected using locking rods (to form a surgical construct), thereby allowing a spinal segment to be fixated for stabilization or fusion.

Additionally, screws for internal fixation can be surgically inserted, either open or percutaneously. If they are inserted open, the skin, muscle, and connective tissue are split and retracted surgically, thereby providing the surgeon with open access to the underlying bone. Screws and other hardware (e.g., to interconnect the screws) may then be implanted into the patient through said access, after which the muscle and skin are re-approximated and surgically closed by using sutures or other methods commonly known in the art.

The most common method for percutaneous insertion of screws for internal fixation is the use of cannulated screws with surgical guide wires. The guide wire, which has a sharp tip that may also be threaded, is mounted to the end of a drill and surgically inserted under fluoroscopic or image guidance until it penetrates through the patient's skin and muscle, and anchors into bone. Additionally, relatively small diameter (e.g., 1.5 mm or less) guide wires are typically used so that they can be disengaged and repositioned without substantially damaging the bone if they do not strike the bone in the desired target. Tools, such as dilators, drills, and taps, that are cannulated are then positioned over the anchored guide wire and forced down into contact with the bone. These tools are used to prepare the hole or opening in the bone to accept the screw. A cannulated screw is then positioned over the guide wire and a cannulated screwdriver is used to insert the screw into the patient's bone, all while the guide wire remains in position. After the screw has been successfully inserted into the patient's bone, the guide wire is removed, and the puncture required to place the guide wire and screw is sealed.

Pins, screws, and rods can also be used for external fixation. In such cases, a portion of the screw and/or pin resides outside of the body, but passes through the skin and muscle to connect to the patient's bone, usually at some distance from the injury or surgical region.

In orthopedics, it is also common to revise a construct (e.g., rods and screws) after it has been in the human body for a period of time. Unfortunately, upon inserting the bone screw or in an effort to remove the bone screw, the proximal head and insertion feature may strip or become unable to be used to continue to advance the bone screw into the bone, or to remove the bone screw from a bone or plate. Being able to prevent the insertion feature from stripping or becoming unusable will save time and effort in the operating room, and be beneficial to both the patient and the surgeon.

Therefore, there is a long felt need in the art for a new and improved bone screw that prevents the insertion feature from stripping, or otherwise becoming unusable during or after a procedure. There is also a long felt need in the art for a bone screw that is capable of serving different purposes at each of its respective ends. More specifically, the distal end and the proximal end of a bone screw are needed to do very different things. The distal end of the bone screw needs to hold the bone together, and not be easily pulled from the bone. By comparison, the proximal end of the bone screw needs to be able to accept more torsional load, and not strip during an insertion or removal procedure. Finally, there is a long felt need in the art for a composite bone screw that is relatively inexpensive to manufacture, and safe and easy to use.

The mixed material bone screw of the present invention, as described in the detailed description below, sets forth an improved bone screw comprised of a plurality of materials to prevent or reduce the likelihood of stripping of the bone screw during its insertion and/or removal. By using different materials for the different sections of the bone screw that require different physical properties, the improved bone screw of the present invention will perform much better in a plurality of different applications and surgical settings.

SUMMARY

The following presents a simplified summary in order to provide a basic understanding of some aspects of the disclosed innovation. This summary is not an extensive overview, and it is not intended to identify key/critical elements or to delineate the scope thereof. Its sole purpose is to present some concepts in a simplified form as a prelude to the more detailed description that is presented later.

The subject matter disclosed and claimed herein, in one aspect thereof, comprises a bone screw manufactured of a plurality of different materials. More specifically, the bone screw comprises a proximal end and a distal end, a screw shaft, a screw head, and a screw tip coupled to the screw shaft. The screw shaft further comprises a screw thread at least partially covering the length of the screw shaft. In some embodiments, the screw shaft is configured and arranged to be at least partially rotated by a screwdriver or other driving force. Further, the distal end of the bone screw is comprised of a biocompatible material, and the proximal end of the bone screw is comprised of a second material that is relatively stronger/stiffer than the first biocompatible material.

In another embodiment of the present invention, the improved bone screw is cannulated, wherein the bone screw has a bore forming a central longitudinal channel that is connected to, or in communication with, one or more sideward or lateral channels. The central longitudinal channel, and the one or more sideward or lateral channels in communication therewith, are useful for delivering bone cement and/or other useful substances into the bone and surrounding the bone screw.

To the accomplishment of the foregoing and related ends, certain illustrative aspects of the disclosed innovation are described herein in connection with the following description and the annexed drawings. These aspects are indicative, however, of but a few of the various ways in which the principles disclosed herein can be employed and is intended to include all such aspects and their equivalents. Other advantages and novel features will become apparent from the following detailed description when considered in conjunction with the drawings.

BRIEF DESCRIPTION OF THE DRAWINGS

The description refers to provided drawings in which similar reference characters refer to similar parts throughout the different views, and in which.

DETAILED DESCRIPTION

Figure 1:
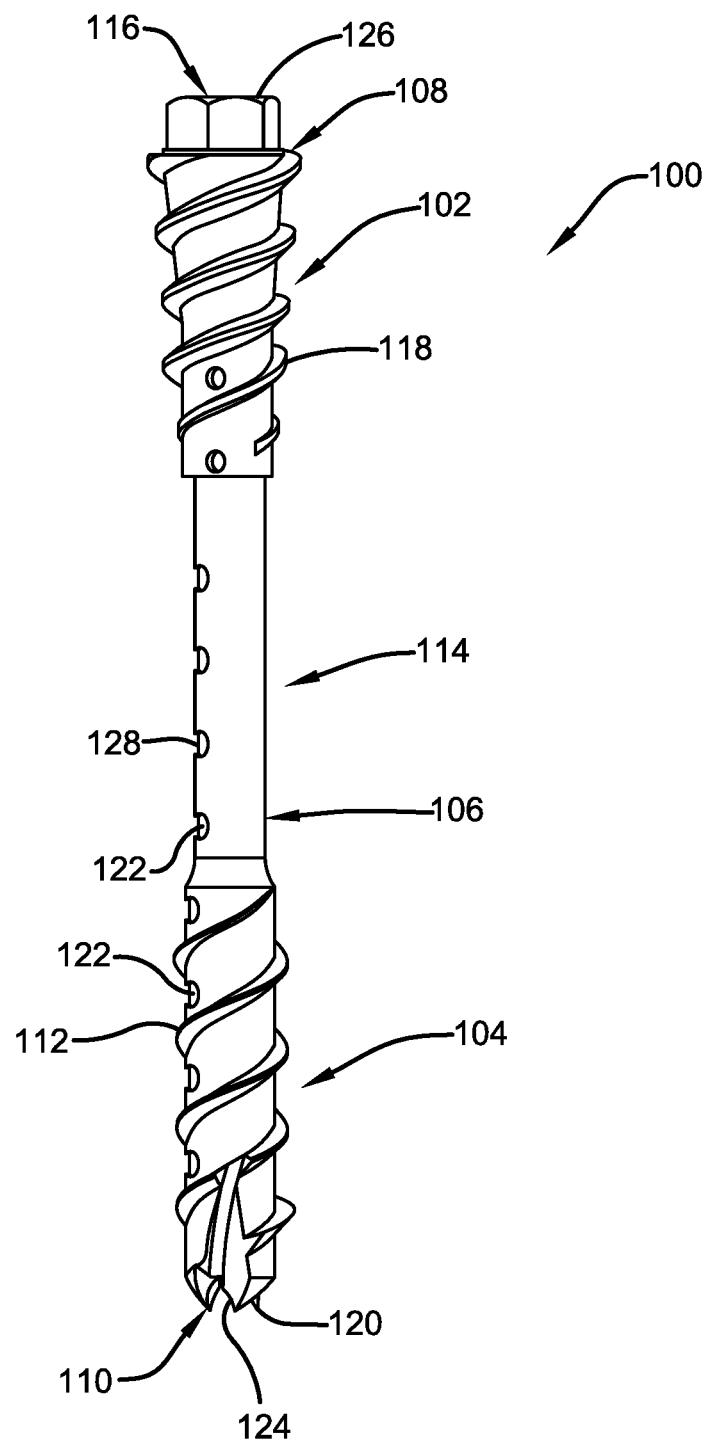
FIG. 1 illustrates a perspective view of one potential embodiment of the improved bone screw of the present invention in accordance with the disclosed architecture, and comprising a plurality of different materials.

The innovation is now described with reference to the drawings, wherein like reference numerals are used to refer to like elements throughout. In the following description, for purposes of explanation, numerous specific details are set forth in order to provide a thorough understanding thereof. It may be evident, however, that the innovation can be practiced without these specific details. In other instances, well-known structures and devices may be shown in block diagram form in order to facilitate a description thereof. Various embodiments are discussed hereinafter. It should be noted that the figures are described only to facilitate the description of the embodiments, and that they are not intended as an exhaustive description of the invention and do not limit the scope of the invention. Additionally, an illustrated embodiment need not have all the aspects or advantages shown. Thus, in other embodiments, any of the features described herein from different embodiments may be combined.

Generally stated, and in one exemplary embodiment thereof, the present invention discloses a mixed material bone screw. More specifically, the bone screw comprises a distal end made of a biocompatible material, and a proximal end made from a second material that is different from, and relatively stronger/stiffer than, the biocompatible material. This second material is capable of better withstanding the torsional forces placed on the bone screw during an insertion or removal procedure, and the use thereof reduces the likelihood of stripping.

In another embodiment of the present invention, the improved bone screw is cannulated, wherein the mixed material bone screw has a bore forming a central longitudinal channel connected to, and in fluid communication with, one or more sideward or lateral channels. The central longitudinal channel, and the one or more sideward or lateral channels in communication therewith, are useful for delivering bone cement or other useful substances into the bone surrounding the improved bone screw following its implantation.

Referring initially to the drawings, FIG. 1 illustrates a perspective view of one potential embodiment of the improved bone screw 100 of the present invention in accordance with the disclosed architecture, and comprising a plurality of different materials. The improved bone screw 100 may be used to reinforce a patient's bones by connecting at least two sections of a bone and/or by holding bone plates or other implants to a bone. More specifically, the improved bone screw 100 depicted in FIG. 1 is a bone screw that is configured to be used as a compression screw to compress two bone pieces together, for example, in the foot of a patient. However, the present invention is not so limited, and the improved bone screw 100 may be any bone screw used in conjunction with any anatomical bone.

In one embodiment, the improved bone screw 100 of the present invention is comprised of a proximal end 102, a center section 114, and a distal end 104. The improved bone screw 100 further comprises a screw shaft 106, a screw head 108, and a screw tip 110 coupled to the screw shaft 106. Furthermore, the screw shaft 106 comprises a first outer screw thread 112 at least partially covering a length of the screw shaft 106. In some embodiments, the screw shaft 106 is configured and arranged to be at least partially rotated by a screwdriver (not shown), or other driving force.

Figure 2:
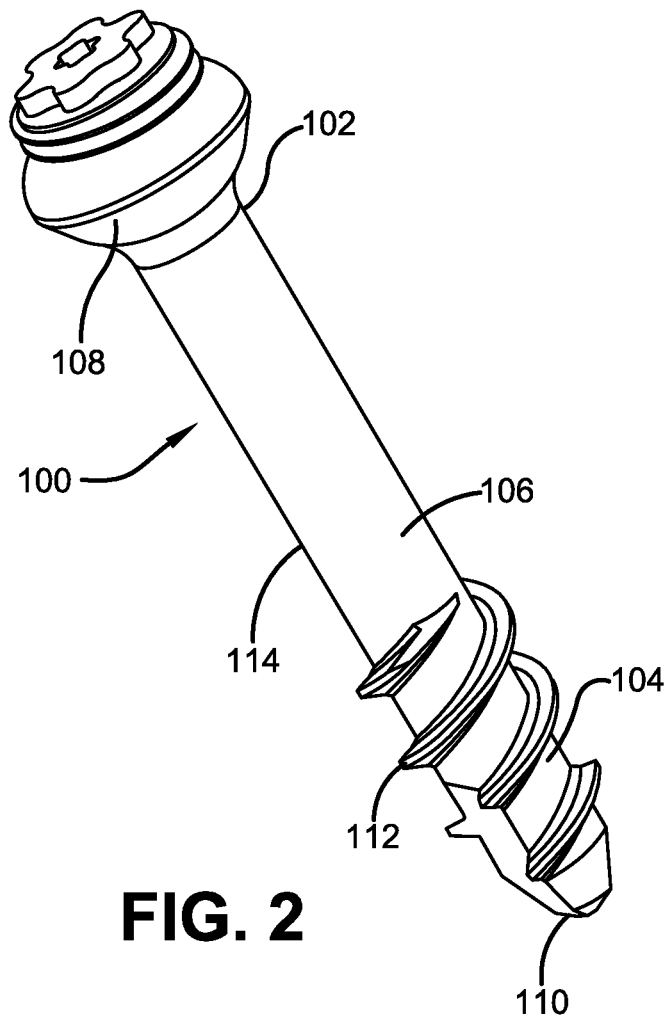
FIG. 2 illustrates a perspective view of one potential embodiment of the mixed material bone screw of the present invention in accordance with the disclosed architecture, and comprising a distal end and a proximal end.

The bone screw 100 is sized and shaped for use with any two bone pieces of the foot, or other lower extremities, although one skilled in the art may use the device of the present invention in other regions of the human anatomy as well. Additionally, the bone screw 100 can be any suitable size, shape, and configuration as is known in the art without affecting the overall concept of the invention. One of ordinary skill in the art will appreciate that the shape, size and configuration of the improved bone screw 100 and its various components as shown in FIGS. 1-2 are for illustrative purposes only, and that many other shapes, sizes and configurations of the improved bone screw 100 and it's various components are well within the scope of the present disclosure. Although the dimensions of the improved bone screw 100 (i.e., length, width, and height) are important design parameters for good performance, the improved bone screw 100 and it's various components may be any shape, size and/or configuration that ensures optimal performance during use.

In one exemplary embodiment, the improved bone screw 100 is comprised of a proximal end 102, a center section 114, and a distal end 104. The distal end 104 has a generally cylindrical shape with a first outer thread 112. An outer thread 112 is a thread positioned on the exterior surface of the screw 100, basically for interfacing with a patient's bone. In an alternate embodiment, the distal end 104 may have a conical shape having a first outer thread 112. This distal end 104 is intended for interfacing with a bone plate, which can be attached by means of the improved bone screw 100 to the surface of a bone (not shown). The screw 100 may also be used for fixing or holding various bone parts together, without using a bone plate. Furthermore, the proximal end 102 has at least one means for driving the improved bone screw 100 (insertion feature), or removing the same.

In one embodiment, the proximal end 102 also has a generally cylindrical shape with a second outer thread 112. Similar to the first outer thread 112, the second outer thread 118 is a thread positioned on the exterior surface of the screw 100, basically for interfacing with a patient's bone. The pitch of the second outer thread 118 of the proximal end 102 is preferably larger than the pitch of the first outer thread 112 of the distal end 104. This difference in pitches allows for tightly fixing a bone plate to a bone, or for tying at least two bone fragments together. Alternatively, both pitches may be the same or similar. Next to the proximal end 102 is a center section 114. The center section 114 has a roughly cylindrical shape, and the diameter of the center section 114 is preferably smaller than the diameter of the proximal end 102, or it can be the same size as the diameter of the proximal end 102. The center section 114 may further comprise an extension of either of the first outer thread 112 or the second outer thread 118, or both, into the center section 114.

At the distal side 104 of the first outer thread 112, there may be at least one cutout 120 for simplifying cutting of the outer thread 112 into the patient's bone, and a distal opening 124 for dispensing bone graft or other materials. Nonetheless, in an alternative embodiment, the distal end 104 of the improved bone screw 100 may have a closed end without a distal opening 124.

Additionally, as previously stated, the improved bone screw 100 of the present invention is preferably manufactured of a plurality of mixed materials. Specifically, the distal end 104 of the improved bone screw 100 is preferably comprised of a first biocompatible material, and the proximal end 102 is preferably comprised of a second biocompatible material that is relatively stiffer/stronger that the first biocompatible material to prevent stripping of the insertion feature of the bone screw 100. For example, the stronger biocompatible material of the proximal end 102 can be cobalt chrome, or a very hardened stainless steel, or any other suitable biocompatible material known in the art to be relatively stronger than titanium. The biocompatible material of the distal end 104 can be a titanium alloy, such as Ti 6Al-4V ELI.

Ti 6Al-4V ELI is one of the most commonly used titanium alloys, and is an alpha-beta alloy containing 6% Al and 4% V, by weight. In the case of medical applications, stringent user specifications require controlled microstructures and freedom from melt imperfections. The interstitial elements of iron and oxygen are carefully controlled to improve ductility and fracture toughness. Controlled interstitial element levels are designated ELI (extra low interstitials).

The two respective ends 102, 104 of the mixed materials bone screw 100 can be mated in many ways. For example, the two respective ends 102, 104 can be mated in traditional ways, via traditional mating features such as a threaded component, a taper lock, welding, or pinning, or any other suitable mating means as is known in the art. Additionally, the distal end 104 can be manufactured in any traditional manufacturing means and then placed into an additive manufacturing center, wherein the proximal end 102 is then printed onto the distal end 104. The mating surface would be such to allow the printer to place material into the distal end 104 to help resist torsional loading. The melt temperature of the material can be such that the mating joint fuses as one part.

The bone screw 100 is typically manufactured in parts, with the distal end 104 being machined, and the proximal end 102 being manufactured using additive manufacturing (AM) techniques. More specifically, the distal end 104 would be machined first, then the proximal end 102 would be additively manufactured as an extension of the distal end in the proximal direction. In AM techniques, fine powders (5-50 μm) are used to build parts layer by layer. The distal end 104 would be machined then placed on the build platform, where a powder spreader then spreads a thin layer of powder on the machined part. The laser then melts the powder in locations where the part (proximal end 102) is to be. When the layer is complete, the build platform is moved downward by the thickness of one layer, and a new layer is spread on the previous layer. The melting and spreading process is repeated as the part is built layer by layer. When complete, the un-melted powder can be recovered and used again. The part (proximal end 102 and distal end 104) can then be heat treated if necessary, and removed from the build platform as one congruent part.

Additionally, the perimeter or edge of the distal end 104 can be jagged or rough, creating valleys and peaks such that when the proximal end 102 is additively manufactured onto the distal end 104, the powder fills in the valleys or jagged indentations to create a strong bond between the distal end 104 and the proximal end 102 to fuse as one part. Instead of a flat surface, the jagged or rough valleys and peaks create a more stable bond between the proximal and distal ends 102, 104 which, in turn, allows the bone screw 100 to be stronger at that site to help resist torsional loading.

In another embodiment, the improved bone screw 100 has a longitudinal channel 116, preferably extending from the proximal end 102 to the distal end 104, wherein the channel 116 defines a center axis. The hollow channel 116 is preferably cylindrical in shape, and has a constant diameter at the center section 114 and the distal end 104. The diameter may be enlarged at the proximal end 102. The center section 114 may also bear at least one or a plurality of sideward or lateral holes or openings 122 in fluid communication with the longitudinal channel 116, which allow the flow of material from the channel 116 or lumen into the bone and surrounding areas.

In another embodiment of the present invention, the channel 116 is provided within each of the proximal end 102, the center section 114, and the distal end 104. The channel 116 preferably has a circular cross section, and a constant diameter. The channel 116 is also connected to the sideward openings 122 and to the distal opening 124 of the distal end 104, and to a proximal opening 126 at the proximal end 102 of the screw 100. The channel 116 may be used to deliver any material, for example a bone cement (permanent or bioresorbable), a bone graft, or a medication into the surrounding bone material. Specifically, delivery of bone cement into a bone material in close proximity of the bone screw 100 may increase the mechanical retention of the bone screw 100 within the bone material.

The side openings 122, which are provided in the center section 114 and/or distal end 104, are provided by pairs resulting in through-holes through the screw 100. Therefore, two side openings 122 are oriented at an approximate 180 degree angle with respect to each other in a plane perpendicular to the center axis of the screw 100. In an alternative embodiment, there may be three or more side openings 122 in the same plane. There may be at least one cutting edge 128 on at least one of the side openings 122. This cutting edge 128 allows cutting of the material or bone cement when removing the screw 100 by rotating counter-clockwise. The angle of the cutting edge 128 is, in one embodiment, less than 90 degrees. The side openings 122 may be oriented into specific directions for directing the flow of material into the bone. They are oriented orthogonally to the center axis or towards the distal end 104 to direct the flow of material into a distal direction.

In use, the bone screw 100 according to the present invention reinforces bones by connecting at least two sections of a bone and/or by holding bone plates or other implants to a bone. The placement of the bone screw 100 in a patient may be pre-operatively determined based on a pre-operative examination of the patient's anatomy using non-invasive imaging techniques known in the art. Next, bone screws 100 are inserted into through holes of the bone plate, or directly into the patient's bone. The bone screws 100 are then driven into the bone via an insertion feature at the proximal end (i.e., means for driving the screw). Further, the difference in pitch between the outer thread at the distal end and the outer thread at the center section allows for tightly fixing a bone plate to a bone or for tying at least two bone fragments together. Additionally, at least one cutout at the distal end simplifies cutting of the outer thread into the bone. Once secure, the bone screws 100 are correctly positioned in the through holes, or in the bone.

To remove the bone screws 100 from a patient, the same instrument is used to rotate the screws 100 in a counter-clockwise direction by an instrument that may be inserted into the patient to remove the bone screws 100. More specifically, the instrument is used to back out the bone screws 100. The stronger/stiffer material used in the proximal end 102 of the improved bone screw 100 allows the bone screw 100 to be removed without stripping.

The bone screw 100 of the present invention provides several advantages over previous designs. For example, the distal end 104 and the proximal end 102 of a bone screw 100 can have different functions in orthopedics. The distal end 104 needs to hold the bone together and not be easily pulled from the bone. Using a material that is compatible with osteointegration can be useful, but most of these materials are not strong enough to resist stripping. The head and insertion features of the bone screw 100 need to be able to accept more torsional loads, and not strip. Using different materials for the different sections of the bone screw 100 that need different physical properties can allow the bone screw 100 to perform better in several different applications. Thus, the disclosed bone screw 100 manufactures the distal end 104 and the proximal end 102 from different materials to take advantage of the different properties of those materials. Accordingly, the distal end 104 of the bone screw 100 can be manufactured from any biocompatible material that is strong enough to resist the loads that are exhibited on the bone screw 100 in the human body. This material can also promote osteointegration so that the bone will grow onto the bone screw 100 to help hold it in place. By comparison, the proximal end 102 of the bone screw 100 is preferably manufactured from a stiffer/stronger material that is biocompatible, and which would also resist stripping of the insertion feature of the bone screw 100.

Figure 3:
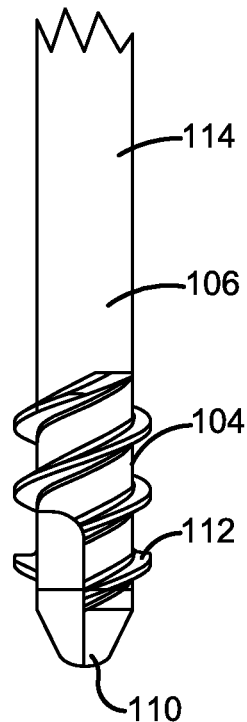
FIG. 3 illustrates a close up perspective view of one potential embodiment of the distal end of the mixed material bone screw of the present invention in accordance with the disclosed architecture.
Figure 4:
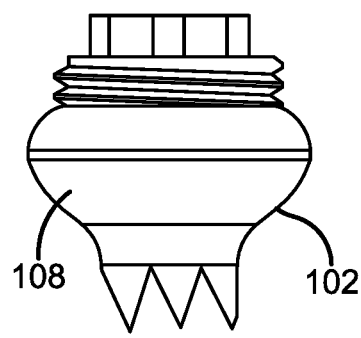
FIG. 4 illustrates a close up perspective view of one potential embodiment of the proximal end of the mixed material bone screw of the present invention in accordance with the disclosed architecture.

FIG. 2 illustrates a perspective view of one potential embodiment of the mixed material bone screw 100 of the present invention in accordance with the disclosed architecture, and comprising a distal end 104 and a proximal end 102. More specifically, the mixed material bone screw 100 of the present invention is comprised of a proximal end 102, a center section 114, and a distal end 104. The improved bone screw 100 further comprises a screw shaft 106, a screw head 108, and a screw tip 110 coupled to the screw shaft 106. Furthermore, the screw shaft 106 comprises a first outer screw thread 112 at least partially covering a length of the screw shaft 106. In some embodiments, the screw shaft 106 is configured and arranged to be at least partially rotated by a screwdriver (not shown), or other driving force. FIG. 3 illustrates a close up perspective view of one potential embodiment of the distal end 104 of the mixed material bone screw 100 of the present invention in accordance with the disclosed architecture, and FIG. 4 illustrates a close up perspective view of one potential embodiment of the proximal end 102 of the mixed material bone screw 100 of the present invention in accordance with the disclosed architecture.

Various modifications and additions can be made to the exemplary embodiments discussed without departing from the scope of the present invention. While the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What has been described above includes examples of the claimed subject matter. It is, of course, not possible to describe every conceivable combination of components or methodologies for purposes of describing the claimed subject matter, but one of ordinary skill in the art may recognize that many further combinations and permutations of the claimed subject matter are possible. Accordingly, the claimed subject matter is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:
1. A bone screw comprising:
a proximal end;
a center section;
a distal end comprising a jagged perimeter;
a screw shaft;
a screw head;
a screw tip comprising at least one cut out and a distal opening, the screw tip coupled to the screw shaft, wherein the screw shaft comprises a first outer screw thread at least partially covering the screw shaft, and further wherein the proximal end is manufactured of a stronger material than the distal end; and
wherein the proximal end is additively manufactured onto the distal end engaging the jagged perimeter of the distal end to bond the proximal end to the distal end; and wherein the proximal and distal ends are heat treated once joined.

2. The bone screw of claim 1, wherein the distal end is comprised of a titanium alloy.

3. The bone screw of claim 2, wherein the titanium alloy is a Ti 6Al-4V ELI.

4. The bone screw of claim 1, wherein the proximal end is comprised of a cobalt chrome.

5. The bone screw of claim 1, wherein the distal end is machined.

6. The bone screw of claim 1 further comprising an internal channel extending from the proximal end to the distal end, wherein the internal channel defines a center axis.

7. The bone screw of claim 6 further comprising a plurality of side openings in fluid communication with the internal channel.

8. The bone screw of claim 7, wherein at least one of the plurality of side openings is comprised of a cutting edge.

* * * * *